United States Patent [19]

Conner et al.

[11] Patent Number: 4,515,774

[45] Date of Patent: May 7, 1985

[54] LIQUID, CINNAMAL DIALKYL MALONATES AS SOLE ORGANIC SUNSCREENS

[75] Inventors: Donald E. Conner, Clifton; Kenneth Klein, Fairlawn, both of N.J.

[73] Assignee: Van Dyk & Company Inc., Belleville, N.J.

[21] Appl. No.: 621,454

[22] Filed: Jun. 18, 1984

[51] Int. Cl.$^3$ ................................................ A61K 7/42
[52] U.S. Cl. .................................... 424/59; 424/168; 424/195.1
[58] Field of Search .......................................... 424/59

[56] References Cited

U.S. PATENT DOCUMENTS 3,215,550 11/1965 Strobel et al. ................... 424/59 X
3,215,724 11/1965 Strobel et al. ................... 424/59 X

FOREIGN PATENT DOCUMENTS 2604554 11/1977 Fed. Rep. of Germany ........ 424/59

*Primary Examiner*—Dale R. Ore
*Attorney, Agent, or Firm*—L. Chasan

[57] ABSTRACT

Non-polar cosmetic oil compositions containing a liquid cinnamal dialkyl malonate are very effective in providing broad spectrum sunscreen protection.

6 Claims, No Drawings

LIQUID, CINNAMAL DIALKYL MALONATES AS SOLE ORGANIC SUNSCREENS

FIELD OF THE INVENTION

Extensive studies have been made of the ultraviolet radiation of sunlight and skylight reaching the surface of the earth and the effects of such radiation on the human skin. It has been established that the radiation between 290 nanometers (nm.) and 320 nanometers produces substantially all of the burning, or erythemal energy, and a substantial portion of the tanning energy, while the between 320 nanometers and 400 nanometers promotes incident tanning. The cosmetic industry has divided these spectra into respectively UV-B, and UV-A. The different intensities and the erythemal and tanning effectiveness of the various wave lengths within these ranges have been established and methods have been determined for calculating accurately their effects on normal untanned skin.

Approximately 76% of the physiological tanning potential of sunlight is found in the ultraviolet range between 290 nanometers and 320 nanometers, the so-called UV-B or erythema area; the balance is found in the range between 320 nanometers and 400 nanometers, the so-called UV-A tanning area.

Typical organic sunscreens such as 2-ethylhexyl para methoxy cinnamate, homomethyl salicylate, p-aminobenzoic acid and its esters, and p-dimethyl amino benzoates, provide protection in the erythemal UV-B area, but lesser protection in the tanning area.

It is becoming increasingly apparent that ultraviolet in the tanning UV-A area can also have determintal effects on skin health, e.g. causing premature aging as well as skin cancer. Accordingly, the need has developed for more effective broad spectrum sun screens to filter out the entire radiation.

The foregoing is discussed further by Lowe "Sunscreen Predictive Assays", Cosmetics and Toiletries, pg. 65 et seq, March 1983. In that article a sun protection factor (SPF) and a correction factor (CF) are utilized:

$$SPF = \frac{\text{Correction Factor}}{\ln \sum_{290}^{320} (\% \, T \times \text{Erythemal Efficiency Spectrum} \times \text{Solar Intensity Spectrum})}$$

Currently employed UVB sunscreens absorb typically in the 290–320 nm range and exhibit a λ max at approximately 310 nm when placed into a polar solvent (Isopropyl Alcohol). Most cosmetic vehicles are emulsions which contain nonpolar materials such as mineral oil. The λ max of these sunscreens in mineral oil is significantly shifted to the shorter wavelengths typically <305 nm. A UV absorber, which shows absorbance above 320 nm, is used to counteract this wavelength shift in nonpolar systems. Thus, to achieve an SPF of 15, Benzophenone-3 is conveniently employed. Because of this shift it is not possible to achieve this level of erythemal protection (SPF 15) with currently available UV absorbers by themselves in nonpolar systems. In fact even if a polar system was used, the absorber exhibits a wavelength shift due to the nonpolar skin lipids.

SUMMARY OF THE INVENTION

It has now been found that certain liquid, cinnamal dialkyl malonates provide minimal shift in λ max in nonpolar cosmetic oil carriers, and based on this and other characteristics, can be used therewith as substantially the sole sunscreen in formulations, and still achieve an SPF of 15.

PRIOR ART

Some malonates have been disclosed as UV absorbers for industrial uses. Typically they are completely unsuitable for cosmetic purpose in human applications, e.g. German Pat. No. 1,087,902. A malonate, diethyl p-dimethylamino-benzalmalonate has been disclosed in U.S. Pat. No. 3,895,104 as a conventional UV absorber in a polyamide resin film, but actually provides substantially no protection, even in the burning range. Ser. No. 404,964, filed Aug. 3, 1982, now U.S. Pat. No. 4,457,911 and Ser. No. 600,080 filed Apr. 13, 1984 utilize dialkyl malonates as adjuvants for other organic sunscreens.

DETAILED DESCRIPTION OF THE INVENTION

The sole sunscreens of this invention are liquid, cinnamal dialkyl malonates corresponding to the formula,

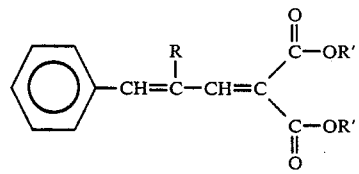

wherein R is selected from the group consisting of hydrogen and an alkyl radical having from 1 to 8 carbon atoms, preferably 1 to 5, and $R^1$ is an alkyl radical having from 1 to 2 carbon atoms.

These compounds are conveniently prepared by reacting the appropriate α-alkyl cinnamic aldehyde with a diester, such as diethyl ester, of malonic acid in a toluene solution containing 0.1 mole of piperidine acetate per mole of aldehyde. After removal of the required amount of water, the batch is washed neutral and the toluene removed under water jet vacuum and the product distilled under high vacuum.

(1) Diethyl α-methyl cinnamal malonate. B.P. 103° C. @ 0.01 mm.

(2) Diethyl α-amyl cinnamal malonate. B.P. 200° C. @ mm.

Those compounds wherein R is methyl or amyl, and $R^1$ is ethyl, are particularly effective and useful.

The overall composition adapted for application to the human skin thus comprises a non-polar cosmetic oil carrier known to the trade, e.g. mineral, vegetable and animal oils and isopropyl myristate with the organic sunscreens of this invention distributed therein. The sunscreen is utilized in an amount sufficient to provide the desired protection for the skin. Typical total amounts of sunscreen comprise up to about 10 wt.% of the composition.

This invention, and properties of the compositions will be better understood by reference to the following examples:

EXAMPLE 1

The minimal shift in λ max for the materials of this invention is exemplified as compared to standard sunscreens.

| Standard UV Screen | Diethyl Alpha Methyl Cinnamal Malonate | |
|---|---|---|
| (Octyldimethyl PABA) | λ-max (nm) | λ-max (nm) |
| Isopropyl alcohol | 310.0 | 308.5 |
| Mineral oil | 301.0 | 307.0 |
|  | SPF | SPF |
| Isopropyl alcohol | 31.91 | 30.93 |
| Mineral oil | 6.47 | 30.66 |

These results demonstrate that the diethyl alpha methyl cinnamal malonate exhibits almost identical "SPF's" in polar and nonpolar systems whereas the standard UV screen shows a significant decrease in SPF from a polar to non-polar system. It is thus possible to achieve an SPF of 15 on the skin with no other sunscreens except the dialkyl cinnamal malonate.

EXAMPLE 2

Very similar results were obtained as in Example 1 by using the diethyl alpha amyl malonate.

These examples demonstrate that the materials of this invention in even small quantities are extremely effective organic sunscreens, and remedy short-comings of conventional ones.

Mixtures of the materials of this invention can be employed where desired.

The advantages of this invention will be apparent to the skilled in the art. Improved, highly effective, novel broad spectrum compositions are made available, utilizing a liquid, cinnamal dialkyl malonate as the sole sunscreen. Since the malonates are liquid they lend themselves to ease of formulation, compared to conventional solid sunscreens. They do not require solubilizers. Additionally, as liquids they are not prone to crystallization on the skin. They are useful for allergic individuals, and those who have developed sensitivity to other sunscreens.

It will be understood that this invention is not limited to the specific examples which have been offered as particular embodiments, and that modifications can be made without departing from the spirit thereof.

What is claimed is:

1. A sunscreening composition adapted for application to the human skin comprising a non-polar cosmetic oil carrier, containing distributed therein an effective amount to provide substantial protection against erythemal and tanning radiation of between 290 and 400 nanometers of a liquid, cinnamal dialkyl malonate corresponding to the formula,

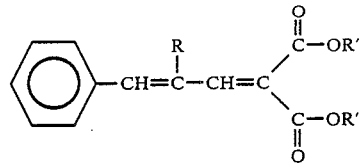

wherein R is selected from the group consisting of hydrogen, and an alkyl radical having from 1 to 8 carbon atoms, and $R^1$ is an alkyl radical having from 1 to 2 carbon atoms, as the sole sunscreen.

2. The composition of claim 1 in which R is methyl and $R^1$ is ethyl.

3. The composition of claim 1 in which R is amyl and $R^1$ is ethyl.

4. A method of protecting the human skin from the effects of erythema and tanning radiation of between 290 and 400 nanometers in sunlight which comprises applying to said skin an effective sunscreening amount of a liquid, cinnamal dialkyl malonate corresponding to the formula,

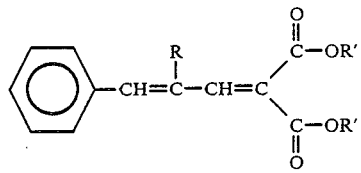

wherein R is selected from the group consisting of hydrogen, and an alkyl radical having from 1 to 2 carbon atoms, and $R^1$ is an alkyl radical having from 1 to 2 carbon atoms, as the sole sunscreen, in a non-polar cosmetic oil carrier.

5. The method of claim 4 in which R is methyl and R' is ethyl.

6. The method of claim 4 in which R is amyl and R' is ethyl.

* * * * *